United States Patent
Osora et al.

(10) Patent No.: US 7,790,914 B2
(45) Date of Patent: Sep. 7, 2010

(54) METHOD FOR DIMETHYL CARBONATE SYNTHESIS

(75) Inventors: Hiroyuki Osora, Hiroshima (JP); Kazuto Kobayashi, Hiroshima (JP); Yoshio Seiki, Hiroshima (JP); Toshinobu Yasutake, Hiroshima (JP); Masaki Iijima, Tokyo (JP); Akira Oguchi, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 12/656,179

(22) Filed: Jan. 20, 2010

(65) Prior Publication Data

US 2010/0121093 A1    May 13, 2010

Related U.S. Application Data

(62) Division of application No. 10/553,267, filed as application No. PCT/JP2004/005457 on Apr. 16, 2004, now Pat. No. 7,674,742.

(30) Foreign Application Priority Data

Apr. 18, 2003  (JP) .............................. 2003-113664

(51) Int. Cl.
*C07C 69/96*  (2006.01)
(52) U.S. Cl. ..................................... 558/277
(58) Field of Classification Search ............... 558/277; 502/240
See application file for complete search history.

(56) References Cited

U.S. PATENT DOCUMENTS

| 5,214,185 A | 5/1993 | Nishihira et al. |
| 5,260,241 A | 11/1993 | Addiego et al. |
| 5,498,744 A | 3/1996 | Jentsch et al. |
| 5,543,548 A | 8/1996 | Landscheidt et al. |
| 5,698,758 A | 12/1997 | Rieser et al. |
| 6,495,733 B1 | 12/2002 | Peratello et al. |

FOREIGN PATENT DOCUMENTS

| EP | 0 634 387 A1 | 1/1995 |
| JP | 6-25104 | 2/1994 |
| JP | 7-69995 | 3/1995 |
| JP | 8-1004 | 1/1996 |
| JP | 10-36297 | 2/1998 |
| JP | 2001-31629 | 2/2001 |
| WO | 00/03801 | 1/2000 |

OTHER PUBLICATIONS

International Search Report issued Aug. 10, 2004 in International (PCT) Application No. PCT/JP2004/005457.
Supplementary European Search Report issued Aug. 10, 2007 in European Application No. 04 72 8019 corresponding to the present application.
Keiichi Tomishige et al., "Catalytic Properties and Structure of Zirconia Catalysts for Direct Synthesis of Dimethyl Carbonate from Methanol and Carbon Dioxide", Journal of Catalysis, Academic Press, Duluth, MN, US, vol. 192, No. 2, Jun. 10, 2000, pp. 355-362, XP005100546.
Yoshiaki Watanabe et al., "Hydrotalcite-type materials as catalysts for the synthesis of dimethyl carbonate from ethylene carbonate and methanol", Microporous and Mesoporous Materials, Elsevier Science Publishing, New York, US, vol. 22, No. 1-3, Jun. 17, 1998, pp. 399-407, XP004128332, ISSN: 1387-1811.
English translation of Office Action dated Feb. 20, 2009 issued in connection with Japanese application No. 2003-113664 corresponding to present U.S. application.

*Primary Examiner*—Kamal A Saeed
(74) *Attorney, Agent, or Firm*—Wenderoth, Lind & Ponack L.L.P.

(57) ABSTRACT

There is provided a catalyst for dimethyl carbonate synthesis which has a high conversion rate under the supercritical condition of $CO_2$ and can be handled easily. The catalyst for dimethyl carbonate is obtained by loading $SO_4^{2-}$ or $PO_4^{3-}$ on a carrier composed of a compound having a solid acid site, and is used to produce dimethyl carbonate from acetone dimethyl carbonate and $CO_2$ in a supercritical state. The component having a solid acid site is preferably one or more of $ZrO_2$, $Al_2O_3$, and $TiO_2$.

6 Claims, No Drawings

US 7,790,914 B2

METHOD FOR DIMETHYL CARBONATE SYNTHESIS

CROSS REFERENCE

This application is a Divisional application of Ser. No. 10/553,267, filed Jul. 12, 2006, now U.S. Pat. No. 7,674,742, which is 371 application of PCT/JP2004/005457, filed Apr. 16, 2004.

TECHNICAL FIELD

The present invention relates to a catalyst for dimethyl carbonate synthesis used to synthesize dimethyl carbonate. More particularly, it relates to a catalyst for dimethyl carbonate synthesis which can be handled easily and which is expected to have a high conversion rate.

BACKGROUND ART

Dimethyl carbonate (hereinafter, also referred to as DMC) is a very useful compound as a fuel additive for increasing the octane value of gasoline etc., as a raw material for polycarbonate, which is an engineering plastic, as a carbonylating agent, or the like. Further, the use of dimethyl carbonate as a raw material for a fuel cell is anticipated. Therefore, the synthesis of dimethyl carbonate has been attempted by using various methods.

As a method for synthesizing dimethyl carbonate, there has conventionally been known a method for obtaining dimethyl carbonate by means of a reaction under a high pressure condition using carbon dioxide and methanol as raw materials. However, because of water yielded at the time of reaction, this method has a problem of low yields and selectivity.

Also, as an industrial manufacturing method, there has generally been known a process for obtaining dimethyl carbonate by means of an esterification reaction using phosgene, which is a highly toxic organic chlorine compound, or carbon monoxide (CO) and methanol as raw materials.

On the other hand, in recent years, a synthesis scheme has been developed for obtaining dimethyl carbonate by using $CO_2$ in a supercritical state and acetone dimethyl acetal (also referred to as 2,2-dimethoxypropane) as raw materials. In such a synthesis scheme, $CO_2$ in a supercritical state is allowed to react with acetone dimethyl acetal over a dibutyltin catalyst under conditions of 30 MPa and 180° C. However, since the dibutyltin catalyst is highly toxic and relatively high in cost, and also because the reaction conditions are tough, it cannot be said that this method is industrially favorable. Furthermore, the yield of dimethyl carbonate in this reaction is about 5%, so that this method is disadvantageous in terms of economy.

As another conventional art, Japanese Patent Provisional Publication No. 6-025104 (No. 025104/1994) has disclosed a method in which dimethyl carbonate is produced continuously by a gas-phase reaction in the presence of a solid catalyst consisting of a platinum-group metal or a compound thereof by using carbon monoxide and methyl nitrite as raw materials. However, this method has a problem of inferior handleability because it uses toxic CO as a raw material.

Japanese Patent Provisional Publication No. 7-069995 (No. 069995/1995) has disclosed a method in which dimethyl carbonate is produced by continuously subjecting carbon monoxide and methyl nitrite to a gas-phase reaction over a heterogeneous catalyst containing a platinum-group metal. However, because this method also uses toxic CO as a raw material, it has a problem of inferior handleability.

Also, Japanese Patent Provisional Publication No. 10-036297 (No. 036297/1998) has disclosed a method in which dimethyl carbonate is produced by transesterification using ethylene carbonate and ethanol. However, since the reaction selectivity is greatly affected by process conditions such as reaction temperature, this method has a problem in that a large-scale system for strictly controlling the reaction conditions is needed.

DISCLOSURE OF THE INVENTION

The present invention has been made to solve the above problems, and accordingly an object thereof is to provide an economical catalyst for dimethyl carbonate synthesis which has a high conversion rate and can be handled easily, the catalyst being used to obtain dimethyl carbonate from acetone dimethyl acetal and $CO_2$ in a supercritical state.

The present invention provides a catalyst for dimethyl carbonate synthesis, which is used for producing dimethyl carbonate from acetone dimethyl acetal and $CO_2$ in a supercritical state, wherein the catalyst is obtained by loading a strong acid on a carrier composed of a compound having a solid acid state.

The catalyst for dimethyl carbonate synthesis is used favorably in the industrial field because it is low in cost and easy to handle, and has a far higher yield of dimethyl carbonate than that of the conventional method. Also, a system for obtaining dimethyl carbonate from methanol and $CO_2$, which is carried out by using this catalyst for dimethyl carbonate synthesis, can be applied to the mass production of dimethyl carbonate because it is clean without discharging unnecessary by-products etc., and has high efficiency.

BEST MODE FOR CARRYING OUT THE INVENTION

An embodiment of the present invention will now be described in detail. However, the present invention is not limited to the embodiment described below.

Hereunder, the present invention will be explained in detail with reference to an embodiment.

According to one embodiment of the present invention, there is provided a catalyst for dimethyl carbonate synthesis which is obtained by loading a strong acid on a carrier composed of a compound having a solid acid site. In a reaction for obtaining dimethyl carbonate from acetone dimethyl acetal and $CO_2$, a catalyst is required that is capable of dehydrating methanol by activated adsorption of $CO_2$.

The phrase "compound having a solid acid site" means various solids in which a solid acid carries out acid-base catalysis, such as meal oxides ($Al_2O_3$, $V_2O_5$, etc.), sulfides (ZnS, etc.), sulfates ($NiSO_4$, $CuSO_4$, etc.), phosphates ($AlPO_4$, Ti phosphate, etc.), chlorides ($AlCl_3$, $CuCl_2$, etc.), clay minerals, and zeolite. In this embodiment, the use of $ZrO_2$, $Al_2O_3$, and $TiO_2$ is especially preferable. This is because each of these compounds has a great specific surface area and a proper acid site, and therefore is effective in stably loading $SO_4^{2-}$ or $PO_4^{3-}$. When these compounds are used as a carrier, they can be used singly or by mixing two or more compounds.

Further, among the compounds having a solid acid site, a compound having a great specific surface area is preferably used. This is because the compound having a great specific surface area has high adsorption power of $CO_2$, which contributes to reaction acceleration. Specifically, a compound having a specific surface area of 40 to 200 $m^2/g$ is preferably used, and the use of a compound having a specific surface area of 70 to 150 $m^2/g$ is further preferable. However, the present invention does not exclude a compound having a specific surface area greater than the above described value.

As a strong acid to be loaded, $SO_4^{2-}$ or $PO_4^{3-}$ is preferably used. However, any strong acid other than the above can be loaded on the aforementioned carrier. As $SO_4^{2-}$ or $PO_4^{3-}$, $SO_4^{2-}$ or $PO_4^{3-}$ derived from $H_2SO_4$, $H_3PO_4$, $(NH_4)_2SO_4$, or $(NH_4)_3PO_4$ can be used.

It is preferable that $SO_4^{2-}$ or $PO_4^{3-}$ of 0.1 to 6% by weight, further preferably 2 to 4% by weight, be loaded on a compound having a solid acid site.

Next, a dimethyl ether modified catalyst in accordance with the present invention is explained by a producing method thereof. A carrier composed of a compound having a solid acid site is prepared as described below.

Specifically, as a carrier, a hydroxide or an oxide containing at least one kind of zirconium (Zr), aluminum (Al), and titanium (Ti) is prepared. The hydroxide or oxide is obtained by adding a salt of said metal(s) to alkali such as aqueous ammonia and precipitating. At this time, the mixing ratio of the salt of said metal to alkali is preferably 1:1 to 1:15, further preferably 1:2 to 1:6, at a molar ratio.

In order to render such a precipitate as an oxide, thermal decomposition of the hydroxide or any other ordinarily used method is carried out. The temperature necessary for the thermal decomposition is 300° C. or higher, and is preferably in the range of 400 to 800° C. so that the carrier can be held stably at the reaction conditions.

As a carrier, any thus prepared hydroxide or oxide having a solid acid site can be used. In particular, oxides such as $ZrO_2$, $Al_2O_3$, and $TiO_2$ are preferably used because catalyst molding can be performed relatively easily and the molding strength can be kept.

As a precursor of $SO_4$ or $PO_4^{3-}$ that is added to the carrier, any substance that is turned into $SO_4^{2-}$ or $PO_4^{3-}$ by calcination at about 500° C. may be used. For example, sulfuric acid, ammonium sulfate, phosphoric acid, ammonium phosphate, and the like can be used. The precursor is not limited to above-described substances.

As a method for adding a catalyst component, there can be adopted, for example, a method in which a carrier composed of a hydroxide or an oxide is immersed in aqueous solution containing a precursor of $SO_4^{2-}$ or $PO_4^{3-}$ at a mol concentration of about 0.01 to 10, preferably about 0.1 to 5, or is impregnated with aqueous solution to perform treatment. Next, the catalyst obtained by loading a strong acid is calcined. As the calcination condition, it is preferable that after being treated by the precursor of $SO_4^{2-}$ or $PO_4^{3-}$, the catalyst be stabilized by the calcination at a temperature of a about 400 to 800° C., preferably about 450 to 700° C., for about 0.5 to 30 hours. The catalyst prepared by the above-described method is a metal oxide containing $SO_4^{2-}$ or $PO_4^{3-}$ and having an acid site.

Next, a synthesis system for dimethyl carbonate using the catalyst for dimethyl carbonate synthesis in accordance with the present invention is explained. Hereunder, a synthesis scheme for dimethyl carbonate is shown.

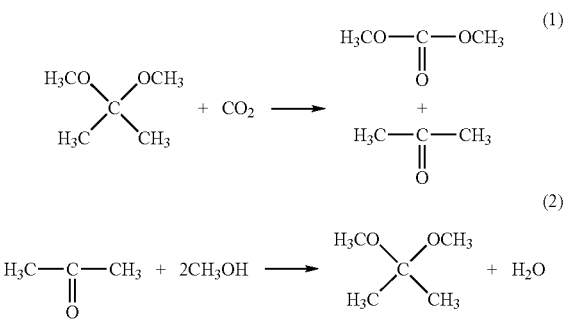

At the system start time, equal mols of acetone dimethyl acetal and $CO_2$ in a supercritical state are required as starting materials. As shown in Formula (1), these materials are allowed to react in the presence of the catalyst for dimethyl carbonate synthesis in accordance with the present invention. By this reaction, intended dimethyl carbonate is yielded at a conversion rate of about 20 to 40%, and at the same time, acetone (dimethyl ketone), which is a side reactant, is yielded.

The critical temperature of carbon dioxide is 31.3° C., and the critical pressure thereof is 7.3 MPa. Therefore, in the reaction using the catalyst in accordance with the present invention, $CO_2$ can be allowed to react with acetone dimethyl acetal under the condition that $CO_2$ is in a supercritical state. Specifically, it is preferable that the reaction using the catalyst of the present invention be carried out in the range of reaction temperature of 150 to 200° C. and reaction pressure of 10 to 30 MPa.

Thus, when the system is brought into normal operation, acetone dimethyl acetal can be produced from acetone, which is a by-product. Therefore, acetone dimethyl acetal itself need not be supplied separately. By supplying $CO_2$ in a supercritical state, which is used for the reaction expressed by Formula (1), and methanol, which is used for the reaction expressed by Formula (2), to the system as occasion calls, the reactions expressed by Formulas (1) and (2) are allowed to proceed, by which dimethyl carbonate can be obtained.

The above-described system using the catalyst for dimethyl carbonate synthesis in accordance with the present invention is a clean system capable of obtaining dimethyl carbonate by using $CO_2$ and methanol, which are low in cost and easy to supply, as raw materials without discharging a by-product that requires separate treatment, so that this system can be used preferably for the industrial mass production of dimethyl carbonate.

More specifically, the synthesis system for dimethyl carbonate using the catalyst for dimethyl carbonate synthesis in accordance with the present invention can be incorporated as a part of a methanol synthesis plant. In this case, $CO_2$ can be obtained from the off-gas of product methanol and methanol synthesis source gas.

EXAMPLES

Next, the present invention is explained in more detail with reference to examples. The following examples do not restrict the present invention.

Example 1

Preparation of Catalyst 1

Two kilograms of zirconium oxychloride ($ZrOCl_2 \cdot 8H_2O$) was dissolved in 15 L of pure water, and aqueous ammonia was dripped gradually until the pH value became 10 while the solution was agitated. After the yielded zirconium hydroxide had been aged for 24 hours, it was filtered, cleaned, and dried in vacuum at 110° C., by which about 800 g of white powder carrier of zirconium hydroxide was obtained. After this carrier of composite metal hydroxide had been immersed in sulfuric acid of 0.5 mol concentration, and excess sulfuric acid had been filtered, the carrier was dried and calcined at 600° C. for three hours, by which Catalyst 1 ($SO_4^{2-}/ZrO_2$) was obtained.

Example 2

Preparation of Catalyst 2

Two kilograms of zirconium oxychloride ($ZrOCl_2 \cdot 8H_2O$) was dissolved in 15 L of pure water, and aqueous ammonia was dripped gradually until the pH value became 10 while the solution was agitated. After the yielded zirconium hydroxide had been aged for 24 hours, it was filtered, cleaned, and dried in vacuum at 110° C., and was further calcined at 650° C., by which about 650 g of white powder carrier of zirconium oxide was obtained. After this carrier of composite metal hydroxide had been immersed in phosphoric acid of 1 mol concentration, and excess phosphoric acid had been filtered, the carrier was dried and calcined at 550° C. for three hours, by which Catalyst 2 ($PO_4^{3-}/ZrO_2$) was obtained.

Example 3

Preparation of Catalyst 3 and Catalyst 4

Catalysts 3 and 4 were obtained by the same method as that in Example 2, except that titanium tetrachloride and aluminum nitrate were used respectively, in place of the zirconium oxychloride used as a carrier component in Example 2.

Example 4

Preparation of Catalyst 5

Two kilograms of commercially available zirconium oxychloride ($ZrOCl_2 \cdot 8H_2O$) and 2.33 kg of aluminum nitrate ($Al(NO_3)_3 \cdot 9H_2O$) were dissolved in 15 L of pure water, and aqueous ammonia was dripped gradually until the pH value became 10 while the solution was agitated. After the yielded zirconium hydroxide/aluminum hydroxide ($Zr(OH)x \cdot Al(OH)x$) composite metal hydroxide had been aged for 24 hours, it was filtered, cleaned, and dried in vacuum at 110° C., by which about 1500 g of white powder carrier was obtained. After this carrier of composite metal hydroxide had been introduced in phosphoric acid of 2 mol concentration, and excess phosphoric acid had been filtered, the carrier was dried and calcined at 550° C. for three hours, by which Catalyst 5 ($PO_4^{3-}/ZrO_2 \cdot Al_2O_3$) was obtained.

Example 5

Preparation of Catalyst 6

Catalyst 6 was obtained by the same method as that in Example 4, except that titanium tetrachloride was used, in place of the zirconium oxychloride used as a carrier component in Example 4.

Comparative Example

Preparation of Comparative Catalyst 1 and Comparative Catalyst 2

The carrier of zirconium oxide prepared in Example 2 was used as Comparative catalyst 1, and the carrier of aluminum oxide prepared in Example 3 was used as Comparative catalyst 2.

The compositions and surface areas of these catalysts are given in Table 1.

TABLE 1

| Composition and surface area of catalyst | | |
|---|---|---|
| Catalyst number | Catalyst composition | Specific surface area ($m^2/g$) |
| Catalyst 1 | $SO_4^{2-}/ZrO_2$ | 45 |
| Catalyst 2 | $PO_4^{3-}/ZrO_2$ | 55 |
| Catalyst 3 | $PO_4^{2-}/TiO_2$ | 61 |
| Catalyst 4 | $PO_4^{3-}/Al_2O_3$ | 102 |
| Catalyst 5 | $PO_4^{2-}/ZrO_2 \cdot Al_2O_3$ | 88 |
| Catalyst 6 | $PO_4^{3-}/TiO_2 \cdot Al_2O_3$ | 95 |
| Comparative catalyst 1 | $ZrO_2$ | 52 |
| Comparative catalyst 2 | $Al_2O_3$ | 105 |

Example 6

Evaluation of Dimethyl Carbonate Synthesis Activity of Catalyst

The dimethyl carbonate synthesis activity was evaluated by using catalysts prepared in Examples 1 to 5 and Comparative example. The synthesis reaction was carried out using an autoclave under the conditions of 185° C., 30 MPa, and 0.5 g of catalyst amount by mixing carbon dioxide ($CO_2$), methanol, and acetone dimethyl acetal (ADA), which are raw materials, so that the amount is 21.3 g, 3.2 g, 3.2 g, respectively. The result was evaluated by the concentration of dimethyl carbonate (DMC) yielded by the reaction. The yield ratio of dimethyl carbonate in the case of reaction using Catalysts 1 to 6 and Comparative catalysts 1 and 2 are given in Table 2 to compare the catalyst activity.

TABLE 2

| Reaction conditions for evaluating catalyst activity and comparison of activity | | | | | | | | |
|---|---|---|---|---|---|---|---|---|
| | Catalyst 1 | Catalyst 2 | Catalyst 3 | Catalyst 4 | Catalyst 5 | Catalyst 6 | Comparative catalyst 1 | Comparative catalyst 2 |
| DMN yield ratio[1) | 0.30 | 1.00 | 0.92 | 0.80 | 0.95 | 0.86 | <0.01 | <0.01 |
| Temperature | | | | 185° C. | | | | |
| Pressure | | | | 30 MPa | | | | |
| Catalyst amount | | | | 0.5 g | | | | |
| Raw materials | | | | 21.3 g/3.2 g/3.2 g | | | | |

[1)Expressed by relative value, taking the yield for the catalyst having the highest activity as 1.

From the results of Table 2, it was found that the yields of the catalysts in accordance with the present invention increase significantly as compared with the yield of the conventional catalysts.

The catalyst for dimethyl carbonate synthesis in accordance with the present invention can be used under the supercritical condition of $CO_2$, and dimethyl carbonate can be obtained from acetone dimethyl acetal and $CO_2$ in a supercritical state at a high conversion rate of about 27%, which is five times or more of the conventional conversion rate. Also, because a solid acid catalyst is used, the catalyst for dimethyl carbonate synthesis in accordance with the present invention has no toxicity unlike the conventional case where phosgene or CO is used, can be handled easily, and further is advantageous in terms of cost.

Furthermore, by using such a catalyst for dimethyl carbonate synthesis, a system can be constructed in which methyl carbonate is yielded by way of acetone dimethyl acetal as a reaction intermediate product and by using methanol and $CO_2$ as raw materials. Because such a system has been incapable of being realized by the conventional method for the reason of reaction equilibrium, the clean system of the present invention is very advantageous in producing dimethyl carbonate industrially. Further, this system can be incorporated in a system for obtaining a raw material for a fuel cell, and therefore is also promising for performing highly efficient operation of a fuel cell.

The invention claimed is:

1. A method for synthesizing dimethyl carbonate comprising the steps of:
    reacting acetone dimethyl acetal with $CO_2$ in supercritical state on a catalyst for dimethyl carbonate synthesis, the catalyst being obtained by loading a strong acid on a carrier composed of a compound having a solid acid site; and
    reacting acetone, which is a by-product of the reaction of acetone dimethyl acetal with $CO_2$, with methanol so as to recycle acetone dimethyl acetal as a raw material.

2. The method for dimethyl carbonate synthesis according to claim 1, wherein the strong acid contains one or more compounds selected from $SO_4^{2-}$ or $PO_4^{3-}$.

3. The method for dimethyl carbonate synthesis according to claim 1, wherein the compound having a solid acid site is one or more selected from $ZrO_2$, $Al_2O_3$, and $TiO_2$.

4. The method for dimethyl carbonate synthesis according to claim 2, wherein the compound having a solid acid site is one or more selected from $ZrO_2$, $Al_2O_3$, and $TiO_2$.

5. The method for dimethyl carbonate synthesis according to claim 3, wherein the specific surface area of the carrier composed of one or more selected from $ZrO_2$, $Al_2O_3$, and $TiO_2$ is 40 to 200 $m^2/g$.

6. The method for dimethyl carbonate synthesis according to claim 4, wherein the specific surface area of the carrier composed of one or more selected from $ZrO_2$, $Al_2O_3$, and $TiO_2$ is 40 to 200 $m^2/g$.

* * * * *